United States Patent [19]
Wu et al.

[11] Patent Number: 6,020,161
[45] Date of Patent: Feb. 1, 2000

[54] PIGR-1, A MEMBER OF IMMUNOGLOBULIN GENE SUPERFAMILY

[75] Inventors: Shujian Wu, Levittown; Raymond W Sweet, Bala Cynwyd; Alemseged Truneh, West Chester; Mark Robert Hurle, Norristown, all of Pa.

[73] Assignee: SmithKline Beecham Corporation, Philadelphia, Pa.

[21] Appl. No.: 08/955,937

[22] Filed: Oct. 22, 1997

Related U.S. Application Data

[60] Provisional application No. 60/056,152, Aug. 19, 1997.

[51] Int. Cl.[7] .............................. C12N 15/00; C12Q 1/68; C07H 21/04; C07K 14/705

[52] U.S. Cl. ........................... 435/69.1; 435/6; 435/70.1; 435/320.1; 435/326; 435/348; 435/354; 435/363; 435/419; 435/252.3; 435/254.11; 536/23.1; 536/23.53

[58] Field of Search ............................. 435/6, 69.1, 70.1, 435/320.1, 326, 348, 354, 363, 419, 252.3, 254.11; 536/23.1, 23.53

[56] References Cited

PUBLICATIONS

GenBank Accession No. X66171 (Aug. 2, 1993).
EST #2175917.
Jackson, David G., et al., "Molecular cloning of a novel member of the immunoglobulin gene homologous to the polymeric immunoglobulin receptor", *Eur. J. Immunol.* 22:1157–1163, (1992).
Danish, A., et al., "Expression of the CMRF–35 antigen, a new member of the immunoglobulin gene superfamily, is differentially regulated on leucocytes", *Immunology* 79:55–63, (1993).

*Primary Examiner*—David Saunders
*Assistant Examiner*—Mary Beth Tung
*Attorney, Agent, or Firm*—William T. Han; Ratner & Prestia; William T. King

[57] ABSTRACT

PIGR-1 polypeptides and polynucleotides and methods for producing such polypeptides by recombinant techniques are disclosed. Also disclosed are methods for utilizing PIGR-1 polypeptides and polynucleotides in the design of protocols for the treatment of rheumatoid arthritis (RA), multiple sclerosis (MS), psoriasis, systemic lupus erythematosus (SLE) and inflammatory bowel disease (IBD), among others and diagnostic assays for such conditions.

18 Claims, No Drawings

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 2345 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
CCGGGTCGAC CCACGCGTCC GTGTGCAGAA GGTGCAAGCC AGAGCTCAGG CAGAACTTCC     60

AGAGTGCATC TGGGATCTGC ATTTGCCACT GGTTGCAGAT CAGGCGGACG AGGAGCCGGG    120

AAGGCAGAGC CATGTGGCTG CCCCCTGCTC TGCTCCTTCT CAGCCTCTCA GGCTGTTTCT    180

CCATCCAAGG CCCAGAGTCT GTGAGAGCCC CAGAGCAGGG GTCCCTGACG GTTCAATGCC    240

ACTATAAGCA AGGATGGGAG ACCTACATTA AGTGGTGGTG CCGAGGGGTG CGCTGGGATA    300

CATGCAAGAT CCTCATTGAA ACCAGAGGGT CGGAGCAAGG AGAGAAGAGT GACCGTGTGT    360

CCATCAAGGA CAATCAGAAA GACCGCACGT TCACTGTGAC CATGGAGGGG CTCAGGCGAG    420

ATGACGCAGA TGTTTACTGG TGTGGGATTG AAAGAAGAGG ACCTGACCTT GGGACTCAAG    480

TGAAAGTGAT TGTTGACCCA GAGGGAGCGG CTTCCACAAC AGCAAGCTCA CCTACCAACA    540

GCAATATGGC AGTGTTCATC GGCTCCCACA AGAGGAACCA CTACATGCTC CTGGTATTTG    600

TGAAGGTGCC CATCTTGCTC ATCTTGGTCA CTGCCATCCT CTGGTTGAAG GGGTCTCAGA    660

GGGTCCCTGA GGAGCCAGGG GAACAGCCTA TCTACATGAA CTTCTCCGAA CCTCTGACTA    720

AAGACATGGC CACTTAGAGA GATGGATCTG CAGAGCCTTC CTGCCCTGGC CACGTTTCCA    780

GAAGAGACTC GGGCTGTGGA AGGAACATCT ACGAGTCCTC GGGATGCAGT GACTGAGATA    840

GGGGCCCTGG GCCTCCGCCC TGGCCTTGGA GCTGGTGGGC ACCTCCCTGT TCTGCACAGC    900

TCAGGGACTT AGCCAGGTCC TCTCCTGAGC CACCATCACC TCCTGGGGTG CCAGCACCTG    960

TTCTCTTGGT CAGGAGCTGT AGAGATGGAG CTCAAGCACT GGACGACTCT GTCCCCACTG   1020

CTGGAATAAC TCGGGCACAG AGCATGGGAC CAAAGTACAG AAAGAGGTTG GGGGAGACCC   1080

CCCCAGCCCT AGACTTCCAT CATTCCGGAG ACCAACTCAA CACCGTCTTT GCCTGAGAAC   1140

CTGATATATC CGTGTTTTTA AATTTTTTTT TTTCTAGCAA AGTTGGGTTT TAATGACTTA   1200
```

```
TGTTCATAGG AAACCTCTCT GATCCCACAC ACAAGGAGGG TGATTCTGGG ATGAGTTCCT   1260

GGTTCTAGGG CATGAGGGGC TGGATGGACC CTGTCCCCAG GGAGGACATG GCTCTGAGTC   1320

CACAGGGCTG AGGAGGCAAT GGGAACCTCC CTGGCCCGGC CCGGTGGTTG GCCTCCCCCT   1380

CCCACCTCTT CCTCCTCCTA GCTCCCCAAG CTCCCTGCCT ATTCCCCCAC CTCCGAGGGG   1440

CTGCAGCTTG GGAGCCTCCT CAGCATGACA GCTTGGGTCT CCTCCCCAAA AGAGCCTGTC   1500

AGGCCTCAAG AACCACCTCC AGGTGGGGAG GGCAGTAACG AAAACCATCG CAGGAAATGG   1560

CACCCTCCCT TTTCGGTGAT GTTGAAATCA TGTTACTAAT GAAAACTGTC CTAGGGAAGT   1620

GGTTCTGTCT CCTCACAGGC TTCACCCACG GCGATGAGGC CCTTGAATGT GGTCACTTTG   1680

TGCTGTATGG TTGAGGGACC CTCACACCAA AGGGACCTTC CCATGTGAGA TGTGCTCCCG   1740

CCCCCACCTG CCCACAAGCA AACACACCAC ACATGTTCGG CATGTTGCCG TTTGAACACC   1800

CATGAGGACG CCTCCAACCT GCTCTTGGTT CTAATAGGGA GTACTGACTG TCAGCAGTGG   1860

ATAAAGGAGA GGGGACCCTC TGGTCCCTAG CATGGCACCC AGAGCCTCCC CTCTTCTTGT   1920

CCTTCAGCCA AAGAGAAACT TTCTCTGACT TTGAACTGAA TTTAGGTCTC TGGCCAATGA   1980

TGGGCCTGAA AATTCCATAA TGGCCAGAGA GGAGAGTTCG AGCCCGGCTA AGATCCCCTG   2040

AGTCATTCTG TGAGGGACCA AGACCCACAG TCCACCAGCC CCAGGGCCCT ACCTCCTGGA   2100

ATGCTTTCCT GGATCCAGCT TCCCGAAGAT CCGACCAGAC CCAGGGAGGA CGGCACCGCT   2160

CCGCGGGAGG GAAAGCCAAA GCATGGTGCT TCACCAGCTG GACTCAGGGG CGAGGGGACA   2220

TGGGCGCTTG TCAACGTGAT GTCATTCTTT TCCCACCGTT TCTTCCTGTT GATATTCAAT   2280

GAATCCGTCA ATCTCTCTGG AAAAAAAAAA AAAAAAAAAA AAAAAAAAAA AAAAAAAAA    2340

AAAAA                                                               2345

(2) INFORMATION FOR SEQ ID NO:2:

(i) SEQUENCE CHARACTERISTICS:
        (A) LENGTH: 201 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Trp Leu Pro Pro Ala Leu Leu Leu Ser Leu Ser Gly Cys Phe
 1               5                  10                  15

Ser Ile Gln Gly Pro Glu Ser Val Arg Ala Pro Glu Gln Gly Ser Leu
            20                  25                  30

Thr Val Gln Cys His Tyr Lys Gln Gly Trp Glu Thr Tyr Ile Lys Trp
        35                  40                  45

Trp Cys Arg Gly Val Arg Trp Asp Thr Cys Lys Ile Leu Ile Glu Thr
    50                  55                  60

Arg Gly Ser Glu Gln Gly Glu Lys Ser Asp Arg Val Ser Ile Lys Asp
65                  70                  75                  80

Asn Gln Lys Asp Arg Thr Phe Thr Val Thr Met Glu Gly Leu Arg Arg
                85                  90                  95

Asp Asp Ala Asp Val Tyr Trp Cys Gly Ile Glu Arg Arg Gly Pro Asp
            100                 105                 110

Leu Gly Thr Gln Val Lys Val Ile Val Asp Pro Glu Gly Ala Ala Ser
        115                 120                 125

Thr Thr Ala Ser Ser Pro Thr Asn Ser Asn Met Ala Val Phe Ile Gly
```

-continued

```
            130                 135                 140
Ser His Lys Arg Asn His Tyr Met Leu Leu Val Phe Val Lys Val Pro
145                 150                 155                 160

Ile Leu Leu Ile Leu Val Thr Ala Ile Leu Trp Leu Lys Gly Ser Gln
                165                 170                 175

Arg Val Pro Glu Glu Pro Gly Glu Gln Pro Ile Tyr Met Asn Phe Ser
                180                 185                 190

Glu Pro Leu Thr Lys Asp Met Ala Thr
                195                 200
```

(2) INFORMATION FOR SEQ ID NO:3:

(i) SEQUENCE CHARACTERISTICS:
        (A) LENGTH: 708 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
TGTGCAGAAG GTGCAAGCCA GAGCTCAGGC AGAACTTCCA GAGTGCATCT GGGATCTGCA    60
TTTGCCACTG GTTGCAGATC AGGCGGACGA GGAGCCGGGA AGGCAGAGCC ATGTGGCTGC   120
CCCCTGCTCT GCTCCTTCTC AGCCTCTCAG GCTGTTTCTC CATCCAAGGC CCAGAGTCTG   180
TGAGAGCCCC AGAGCAGGGG TCCCTGACGG TTCAATGCCA CTATAAGCAA GGATGGGAGA   240
CCTACATTAA GTGGTGGTGC CGAGGGGTGC GCTGGGATAC ATGCAAGATC CTCATTGAAA   300
CCAGAGGGTC GGAGCAAGGA GAGAAGAGTG ACCGTGTGTC CATCAAGGAC AATCAGAAAG   360
ACCGCACGTT CACTGTGACC ATGGAGGGGC TCAGGCGAGA TGACGCAGAT GTTTACTGGT   420
GTGGGATTGA AGAAGAGGA CCTGACCTTG GGACTCAAGT GAAAATTGAT TGTTNACCCA   480
GAGGGAGCGG CTTTCCACAA CAGCAAAGCT CACCTACCAA CAGCAATATG GCAGTGTTCA   540
TCGGCTCCCA CAAGAGGAAC CACTACATGC TCCTGGTATT TGTGAAGGTG CCCATCTTGC   600
TCATCTTGGT CAATGCCATN CTCTGGTTGA AAGGGTCTCA GAGGGTCCCT GAGGAGCCAN   660
GGGAACAGCC TATCTACATG GACTTCTCCG GACTCTGACT AAAGACAT              708
```

(2) INFORMATION FOR SEQ ID NO:4:

(i) SEQUENCE CHARACTERISTICS:
        (A) LENGTH: 195 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Trp Leu Pro Pro Ala Leu Leu Leu Ser Leu Ser Gly Cys Phe
1                   5                  10                  15

Ser Ile Gln Gly Pro Glu Ser Val Arg Ala Pro Glu Gln Gly Ser Leu
                20                  25                  30

Thr Val Gln Cys His Tyr Lys Gln Gly Trp Glu Thr Tyr Ile Lys Trp
                35                  40                  45

Trp Cys Arg Gly Val Arg Trp Asp Thr Cys Lys Ile Leu Ile Glu Thr
                50                  55                  60

Arg Gly Ser Glu Gln Gly Glu Lys Ser Asp Arg Val Ser Ile Lys Asp
65                  70                  75                  80
```

```
Asn Gln Lys Asp Arg Thr Phe Thr Val Thr Met Glu Gly Leu Arg Arg
                85                  90                  95
Asp Asp Ala Asp Val Tyr Trp Cys Gly Ile Glu Arg Arg Gly Pro Asp
            100                 105                 110
Leu Gly Thr Gln Val Lys Ile Asp Cys Xaa Pro Arg Gly Ser Gly Phe
        115                 120                 125
Pro Gln Gln Gln Ser Ser Pro Thr Asn Ser Asn Met Ala Val Phe Ile
    130                 135                 140
Gly Ser His Lys Arg Asn His Tyr Met Leu Leu Val Phe Val Lys Val
145                 150                 155                 160
Pro Ile Leu Leu Ile Leu Val Asn Ala Xaa Leu Trp Leu Lys Gly Ser
                165                 170                 175
Gln Arg Val Pro Glu Glu Pro Xaa Glu Gln Pro Ile Tyr Met Asp Phe
            180                 185                 190
Ser Gly Leu
        195
```

(2) INFORMATION FOR SEQ ID NO:5:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Ile Phe Gly Pro Glu Glu Val Asn Ser Val Glu Gly Asn Ser Val Ser
 1               5                  10                  15
Ile Thr Cys Tyr Tyr Pro Pro Thr Ser Val Asn Thr Arg Lys Tyr Trp
                20                  25                  30
Cys Arg Gln Gly Ala Arg Gly Cys Ile Thr Leu Ile Ser Ser Glu Gly
        35                  40                  45
Tyr Val Ser Ser Lys Tyr Ala Gly Arg
    50                  55
```

(2) INFORMATION FOR SEQ ID NO:6:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Pro Arg Ser Pro Thr Val Val Lys Gly Val Ala Gly Ser Ser Val Ala
 1               5                  10                  15
Val Leu Cys Pro Tyr Asn Arg Lys Glu Ser Lys Ser Ile Lys Tyr Trp
                20                  25                  30
Cys Leu Trp Glu Gly Ala Gln Asn Gly Arg Cys Pro Leu Leu Val Asp
        35                  40                  45
Ser Glu Gly Trp Val Lys Ala Gln Tyr Glu Gly Arg
    50                  55                  60
```

(2) INFORMATION FOR SEQ ID NO:7:

(i) SEQUENCE CHARACTERISTICS:
        (A) LENGTH: 57 amino acids

```
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:7:

Leu Ser His Pro Met Thr Val Ala Gly Pro Val Gly Gly Ser Leu Ser
1               5                   10                  15

Val Gln Cys Arg Tyr Glu Lys Glu His Arg Thr Leu Asn Lys Phe Trp
                20                  25                  30

Cys Arg Pro Pro Gln Ile Leu Arg Cys Asp Lys Ile Val Glu Thr Lys
            35                  40                  45

Gly Ser Ala Gly Lys Arg Asn Gly Arg
    50                  55

(2) INFORMATION FOR SEQ ID NO:8:

(i) SEQUENCE CHARACTERISTICS:
            (A) LENGTH: 59 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:8:

Ser Gln Lys Pro Ser Arg Asp Ile Cys Gln Arg Gly Thr Ser Leu Thr
1               5                   10                  15

Ile Gln Cys Gln Val Asp Ser Gln Val Thr Met Met Phe Trp Tyr Arg
                20                  25                  30

Gln Gln Pro Gly Gln Ser Leu Thr Leu Ile Ala Thr Ala Asn Gln Gly
            35                  40                  45

Ser Glu Ala Thr Tyr Glu Ser Gly Phe Val Ile
    50                  55

(2) INFORMATION FOR SEQ ID NO:9:

(i) SEQUENCE CHARACTERISTICS:
            (A) LENGTH: 55 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:9:

Thr Gln Thr Pro Ala Ser Val Glu Val Ala Val Gly Gly Thr Val Thr
1               5                   10                  15

Ile Lys Cys Gln Ala Ser Gln Ser Ile Ser Thr Tyr Leu Ser Trp Tyr
                20                  25                  30

Gln Gln Lys Pro Gly Gln Arg Pro Lys Leu Leu Ile Tyr Arg Ala Ser
            35                  40                  45

Thr Leu Ala Ser Gly Val Ser
    50                  55

(2) INFORMATION FOR SEQ ID NO:10:

(i) SEQUENCE CHARACTERISTICS:
            (A) LENGTH: 46 amino acids
            (B) TYPE: amino acid
            (C) STRANDEDNESS: single
            (D) TOPOLOGY: linear
```

-continued (ii) MOLECULE TYPE: protein (xi) SEQUENCE DESCRIPTION: SEQ ID NO:10:

Ala Asn Leu Thr Asn Phe Pro Glu Asn Gly Thr Phe Thr Val Ile Leu
 1               5                  10                  15

Asn Gln Leu Ser Gln Asp Asp Ser Gly Arg Tyr Lys Cys Gly Leu Gly
            20                  25                  30

Ile Asn Ser Arg Gly Leu Ser Phe Asp Val Ser Leu Glu Val
        35                  40                  45

(2) INFORMATION FOR SEQ ID NO:11:

(i) SEQUENCE CHARACTERISTICS:
       (A) LENGTH: 43 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:11:

Leu Ser Leu Leu Glu Glu Pro Gly Asn Gly Thr Phe Thr Val Ile Leu
 1               5                  10                  15

Asn Gln Leu Thr Ser Arg Asp Ala Gly Phe Tyr Trp Cys Leu Thr Asn
            20                  25                  30

Gly Asp Thr Leu Trp Arg Thr Thr Val Glu Ile
        35                  40

(2) INFORMATION FOR SEQ ID NO:12:

(i) SEQUENCE CHARACTERISTICS:
       (A) LENGTH: 46 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:12:

Val Ser Ile Arg Asp Ser Pro Ala Asn Leu Ser Phe Thr Val Thr Leu
 1               5                  10                  15

Glu Asn Leu Thr Glu Glu Asp Ala Gly Thr Tyr Trp Cys Gly Val Asp
            20                  25                  30

Thr Pro Trp Leu Arg Asp Phe His Asp Pro Ile Val Glu Val
        35                  40                  45

(2) INFORMATION FOR SEQ ID NO:13:

(i) SEQUENCE CHARACTERISTICS:
       (A) LENGTH: 44 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:13:

Asp Lys Phe Pro Ile Ser Arg Pro Asn Leu Thr Phe Ser Thr Leu Thr
 1               5                  10                  15

Val Ser Asn Met Ser Pro Glu Asp Ser Ser Ile Tyr Leu Cys Ser Val
            20                  25                  30

Glu Gly Glu Ala Gly Asp Thr Gln Tyr Phe Gly Pro
        35                  40

```
(2) INFORMATION FOR SEQ ID NO:14:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

Ser Arg Phe Lys Gly Ser Gly Ser Gly Thr Glu Phe Thr Leu Thr Ile
1               5                   10                  15

Ser Gly Val Glu Cys Ala Asp Ala Ala Thr Tyr Tyr Cys Gln Gln Gly
            20                  25                  30

Trp Ser Ser Ser Asn Val Glu Asn Val Phe Gly
        35                  40
```

PIGR-1, A MEMBER OF IMMUNOGLOBULIN GENE SUPERFAMILY

This application claims the benefit of U.S. Provisional Application No. 60/056,152, filed Aug. 19, 1997.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to Immunoglobulin superfamily, hereinafter referred to as PIGR-1. The invention also relates to inhibiting or activating the action of such polynucleotides and polypeptides.

BACKGROUND OF THE INVENTION

The immunoglobulin (Ig) gene superfamily comprises a large number of cell surface glycoproteins that share sequence homology with the V and C domains of antibody heavy and light chains. These molecules function as receptors for antigen, immunoglobulin and cytokines as well as adhesion molecules (A. F. Williams et al., Annu. Rev. Immunol. 6:381–405, 1988).

Most Ig superfamily members are relatively complex polydomain molecules containing multiple Ig V- and C-like domains (T. Hunkapiller et al., Adv. Immunol. 44:1–63, 1989). However, a subset of them have relatively simple structures containing only a single Ig domain in the extracellular region. Examples of this type of receptors are CD28 and CD8 (A. Aruffo et al., Proc. Natl. Acad. Sci. USA 84:8573–8577, 1987). Recently, CMRF-35, an novel membrane glycoprotein of the Ig gene superfamily containing a single extracellular Ig V domain, was identified by D. G. Jackson et al., Eur. J. Immunol. 22:1157–1163, 1992. CMRF-35 is exclusively detected on cells from both the myeloid and lymphoid differentiation pathways. However, expression of this gene is markedly influenced by stimulation of lcucocytes with mitogens and cytokines (A. Daish et al., Immunology 79:55–63, 1993).This suggests that CMRF-35 may be strongly associated with differentiation and proliferation of diverse leucocytes types. This indicates that these receptors have an established, proven history as therapeutic targets. Clearly there is a need for identification and characterization of further receptors which can play a role in preventing, ameliorating or correcting dysfunctions or diseases, including, but not limited to, rheumatoid arthritis (RA), multiple sclerosis (MS), psoriasis, systemic lupus erythematosus (SLE) and Inflammatory Bowel Disease (IBD).

SUMMARY OF THE INVENTION

In one aspect, the invention relates to PIGR-1 polypeptides and recombinant materials and methods for their production. Another aspect of the invention relates to methods for using such PIGR-1 polypeptides and polynucleotides. Such uses include the treatment of rheumatoid arthritis (RA), multiple sclerosis (MS), psoriasis, systemic lupus erythematosus (SLE) and inflammatory bowel disease (IBD), among others. In still another aspect, the invention relates to methods to identify agonists and antagonists using the materials provided by the invention, and treating conditions associated with PIGR-1 imbalance with the identified compounds. Yet another aspect of the invention relates to diagnostic assays for detecting diseases associated with inappropriate PIGR-1 activity or levels.

DESCRIPTION OF THE INVENTION

Definitions

The following definitions are provided to facilitate understanding of certain terms used frequently herein.

"PIGR-1" refers, among others, to a polypeptide comprising the amino acid sequence set forth in SEQ ID NO:2, or an allelic variant thereof.

"Receptor Activity" or "Biological Activity of the Receptor" refers to the metabolic or physiologic function of said PIGR-1 including similar activities or improved activities or these activities with decreased undesirable side-effects. Also included are antigenic and immunogenic activities of said PIGR-1.

"PIGR-1 gene" refers to a polynucleotide comprising the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Post-translational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S. F. et al., *J Molec Biol* (1990) 215:403).

As an illustration, by a polynucleotide having a nucleotide sequence having at least, for example, 95% "identity" to a reference nucleotide sequence of SEQ ID NO: 1 is intended that the nucleotide sequence of the polynucleotide is identical to the reference sequence except that the polynucleotide sequence may include up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to PIGR-1 polypeptides (or PIGR-1 proteins). The PIGR-1 polypeptides include the polypeptides of SEQ ID NOS:2 and 4; as well as polypeptides comprising the amino acid sequence of SEQ ID NO:2; and polypeptides comprising the amino acid sequence which have at least 80% identity to that of SEQ ID NO:2 over its entire length, and still more preferably at least 90% identity, and even still more preferably at least 95% identity to SEQ ID NO: 2. Furthermore, those with at least 97–99% are highly preferred. Also included within PIGR-1 polypeptides are polypeptides having the amino acid sequence which have at least 80% identity to the polypeptide having the amino acid sequence of SEQ ID NO: 2 over its entire length, and still more preferably at least 90% identity, and even still more preferably at least 95% identity to SEQ ID NO: 2. Furthermore, those with at least 97–99% are highly preferred. Preferably PIGR-1 polypeptides exhibit at least one biological activity of the receptor.

The PIGR-1 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the PIGR-1 polypeptides are also included in the invention. A fragment is a polypeptide having an amino acid sequence that entirely is the same as part, but not all, of the amino acid sequence of the aforementioned PIGR-1 polypeptides. As with PIGR-1 polypeptides, fragments may be "free-standing," or comprised within a larger polypeptide of which they form a part or region, most preferably as a single continuous region. Representative examples of polypeptide fragments of the invention, include, for example, fragments from about amino acid number 1-20, 21-40, 41-60, 61-80, 81-100, and 101 to the end of PIGR-1 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of PIGR-1 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate receptor activity, including those with a similar activity or an improved activity, or with a decreased undesirable activity. Also included are those that are antigenic or immunogenic in an animal, especially in a human.

Preferably, all of these polypeptide fragments retain the biological activity of the receptor, including antigenic activity. Among the most preferred fragment is that having the amino acid sequence of SEQ ID NO: 4. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5-10, 1-5, or 1-2 amino acids are substituted, deleted, or added in any combination.

The PIGR-1 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to PIGR-1 polynucleotides. PIGR-1 polynucleotides include isolated polynucleotides which encode the PIGR-1 polypeptides and fragments, and polynucleotides closely related thereto. More specifically, PIGR-1 polynucleotide of the invention include a polynucleotide comprising the nucleotide sequence contained in SEQ ID NO: 1 encoding a PIGR-1 polypeptide of SEQ ID NO: 2, and polynucleotides having the particular sequences of SEQ ID NOS: 1 and 3. PIGR-1 polynucleotides further include a polynucleotide comprising a nucleotide sequence that has at least 80% identity over its entire length to a nucleotide sequence encoding the PIGR-1 polypeptide of SEQ ID NO:2, and a polynucleotide comprising a nucleotide sequence that is at least 80% identical to that of SEQ ID NO:1 over its entire length. In this regard, polynucleotides at least 90% identical are particularly preferred, and those with at least 95% are especially preferred. Furthermore, those with at least 97% are highly preferred and those with at least 98-99% are most highly preferred, with at least 99% being the most preferred. Also included under PIGR-1 polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such PIGR-1 polynucleotides.

PIGR-1 of the invention is structurally related to other proteins of the Immunoglobulin superfamily, as shown by the results of sequencing the cDNA encoding human PIGR-1. The cDNA sequence of SEQ ID NO:1 contains an open reading frame (nucleotide number 132 to 734) encoding a polypeptide of 201 amino acids of SEQ ID NO:2. The amino acid sequence of Table 2 (SEQ ID NO:2) has about 42.65% identity (using BLASTX) in 67 amino acid residues with CMRF35 (D. G. Jackson et al., Eur. J. Immunol. 22:1157–1163, 1992). Furthermore, PIGR-1 (SEQ ID NO:2) is 30% identical to the poly-Ig receptor over 90 amino acid residues (P. Krajci et al., Biochem. Biophys. Res. Commun. 158:783–789, 1989). The nucleotide sequence of Table 1 (SEQ ID NO:1) has about 68.64% identity (using BLASTN) in 118 nucleotide residues with Hunan CMRF35 mRNA (D. G. Jackson et al., Eur. J. Immunol. 22:1157–1163, 1992). Thus, PIGR-1 polypeptides and polynucleotides of the present invention are expected to have, inter alia, similar biological functions/properties to their homologous polypeptides and polynucleotides, and their utility is obvious to anyone skilled in the art.

TABLE 1[a]

```
   1  CCGGTCGAC CCACGCGTCC GTGTGCAGAA GGTGCAAGCC AGAGCTCAGG
  51  CAGAACTTCC AGAGTGCATC TGGGATCTGC ATTTGCCACT GGTTGCAGAT
 101  CAGGCGGACG AGGAGCCGGG AAGGCAGAGC CATGTGGCTG CCCCCTGCTC
 151  TGCTCCTTCT CAGCCTCTCA GGCTGTTTCT CCATCCAAGG CCCAGAGTCT
 201  GTGAGAGCCC CAGAGCAGGG GTCCCTGACG GTTCAATGCC ACTATAAGCA
 251  AGGATGGGAG ACCTACATTA AGTGGTGGTG CCGAGGGGTG CGCTGGGATA
 301  CATGCAAGAT CCTCATTGAA ACCAGAGGGT CGGAGCAAGG AGAGAAGAGT
 351  GACCGTGTGT CCATCAAGGA CAATCAGAAA GACCGCACGT TCACTGTGAC
 401  CATGGAGGGG CTCAGGCGAG ATGACGCAGA TGTTTACTGG TGTGGGATTG
 451  AAAGAAGAGG ACCTGACCTT GGGACTCAAG TGAAAGTGAT TGTTGACCCA
 501  GAGGGAGCGG CTTCCACAAC AGCAAGCTCA CCTACCAACA GCAATATGGC
 551  AGTGTTCATC GGCTCCCACA AGAGGAACCA CTACATGCTC CTGGTATTTG
 601  TGAAGGTGCC CATCTTGCTC ATCTTGGTCA CTGCCATCCT CTGGTTGAAG
 651  GGGTCTCAGA GGGTCCCTGA GGAGCCAGGG GAACAGCCTA TCTACATGAA
 701  CTTCTCCGAA CCTCTGACTA AGACATGGC CACTTAGAGA GATGGATCTG
 751  CAGAGCCTTC CTGCCCTGGC CACGTTTCCA GAAGAGACTC GGGCTGTGGA
 801  AGGAACATCT ACGAGTCCTC GGGATGCAGT GACTGAGATA GGGGCCCTGG
 851  GCCTCCGCCC TGGCCTTGGA GCTGGTGGGC ACCTCCCTGT TCTGCACAGC
 901  TCAGGGACTT AGCCAGGTCC TCTCCTGAGC CACCATCACC TCCTGGGGTG
 951  CCAGCACCTG TTCTCTTGGT CAGGAGCTGT AGAGATGGAG CTCAAGCACT
1001  GGACGACTCT GTCCCCACTG CTGGAATAAC TCGGGCACAG AGCATGGGAC
1051  CAAAGTACAG AAAGAGGTTG GGGGAGACCC CCCCAGCCCT AGACTTCCAT
1101  CATTCCGGAG ACCAACTCAA CACCGTCTTT GCCTGAGAAC CTGATATATC
1151  CGTGTTTTTA AATTTTTTTT TTTCTAGCAA AGTTGGGTTT TAATGACTTA
1201  TGTTCATAGG AAACCTCTCT GATCCCACAC ACAAGGAGGG TGATTCTGGG
1251  ATGAGTTCCT GGTTCTAGGG CATGAGGGGC TGGATGGACC CTGTCCCCAG
1301  GGAGGACATG GCTCTGAGTC CACAGGGCTG AGGAGGCAAT GGGAACCTCC
1351  CTGGCCCGGC CCGGTGGTTG GCCTCCCCCT CCCACCTCTT CCTCCTCCTA
1401  GCTCCCCAAG CTCCCTGCCT ATTCCCCCAC CTCCGAGGGG CTGCAGCTTG
1451  GGAGCCTCCT CAGCATGACA GCTTGGGTCT CCTCCCCAAA AGAGCCTGTC
1501  AGGCCTCAAG AACCACCTCC AGGTGGGGAG GGCAGTAACG AAAACCATCG
1551  CAGGAAATGG CACCCTCCCT TTTCGGTGAT GTTGAAATCA TGTTACTAAT
1601  GAAAACTGTC CTAGGGAAGT GGTTCTGTCT CCTCACAGGC TTCACCCACG
1651  GCGATGAGGC CCTTGAATGT GGTCACTTTG TGCTGTATGG TTGAGGGACC
1701  CTCACACCAA AGGGACCTTC CCATGTGAGA TGTGCTCCCG CCCCCACCTG
1751  CCCACAAGCA AACACACCAC ACATGTTCGG CATGTTGCCG TTTGAACACC
1801  CATGAGGACG CCTCCAACCT GCTCTTGGTT CTAATAGGGA GTACTGACTG
1851  TCAGCAGTGG ATAAAGGAGA GGGGACCCTC TGGTCCCTAG CATGGCACCC
1901  AGAGCCTCCC CTCTTCTTGT CCTTCAGCCA AAGAGAAACT TTCTCTGACT
1951  TTGAACTGAA TTTAGGTCTC TGGCCAATGA TGGGCCTGAA AATTCCATAA
```

TABLE 1ª-continued

```
2001  TGGCCAGAGA GGAGAGTTCG AGCCCGGCTA AGATCCCCTG AGTCATTCTG

2051  TGAGGGACCA AGACCCACAG TCCACCAGCC CCAGGGCCCT ACCTCCTGGA

2101  ATGCTTTCCT GGATCCAGCT TCCCGAAGAT CCGACCAGAC CCAGGGAGGA

2151  CGGCACCGCT CCGCGGGAGG GAAAGCCAAA GCATGGTGCT TCACCAGCTG

2201  GACTCAGGGG CGAGGGGACA TGGGCGCTTG TCAACGTGAT GTCATTCTTT

2251  TCCCACCGTT TCTTCCTGTT GATATTCAAT GAATCCGTCA ATCTCTCTGG

2301  AAAAAAAAAA AAAAAAAAAA AAAAAAAAAA AAAAAAAAAA AAAAA
```
ªA nucleotide sequence of a human PIGR-1 (SEQ ID NO: 1).

TABLE 2ᵇ

```
  1  MWLPPALLLL SLSGCFSIQG PESVRAPEQG SLTVQCHYKQ GWETYIKWWC

51  RGVRWDTCKI LIETRGSEQG EKSDRVSIKD NQKDRTFTVT MEGLRRDDAD

101  VYWCGIERRG PDLGTQVKVI VDPEGAASTT ASSPTNSNMA VFIGSHKRNH

151  YMLLVFVKVP ILLILVTAIL WLKGSQRVPE EPGEQPIYMN FSEPLTKDMA

201  T
```
ᵇAn amino acid sequence of a human PIGR-1 (SEQ ID NO: 2).

One polynucleotide of the present invention encoding PIGR-1 may be obtained using standard cloning and screening, from a cDNA library derived from mRNA in cells of human bone marrow, macrophage, eosinophil, activated neutrophils and T cells using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding PIGR-1 polypeptide of SEQ ID NO:2 may be identical to the polypeptide encoding sequence contained in Table 1 (nucleotide number 132 to 734 of SEQ ID NO: 1), or it may be a sequence, which as a result of the redundancy (degeneracy) of the genetic code, also encodes the polypeptide of SEQ ID NO:2.

When the polynucleotides of the invention are used for the recombinant production of PIGR-1 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989)86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding PIGR-1 variants comprising the amino acid sequence of PIGR-1 polypeptide of Table 2 (SEQ ID NO:2) in which several, 5-10, 1-5, 1-3, 1-2 or 1 amino acid residues are substituted, deleted or added, in any combination. Among the preferred polynucleotides of the present invention is contained in Table 3 (SEQ ID NO: 3) encoding the amino acid sequence of Table 4 (SEQ ID NO: 4).

TABLE 3ᶜ

```
  1  TGTGCAGAAG GTGCAAGCCA GAGCTCAGGC AGAACTTCCA GAGTGCATCT

51  GGGATCTGCA TTTGCCACTG GTTGCAGATC AGGCGGACGA GGAGCCGGGA

101  AGGCAGAGCC ATGTGGCTGC CCCCTGCTCT GCTCCTTCTC AGCCTCTCAG

151  GCTGTTTCTC CATCCAAGGC CCAGAGTCTG TGAGAGCCCC AGAGCAGGGG

201  TCCCTGACGG TTCAATGCCA CTATAAGCAA GGATGGGAGA CCTACATTAA

251  GTGGTGGTGC CGAGGGGTGC GCTGGGATAC ATGCAAGATC CTCATTGAAA

301  CCAGAGGGTC GGAGCAAGGA GAGAAGAGTG ACCGTGTGTC CATCAAGGAC
```

TABLE 3ᶜ-continued

| | | | | |
|---|---|---|---|---|
| 351 | AATCAGAAAG | ACCGCACGTT | CACTGTGACC | ATGGAGGGGC TCAGGCGAGA |
| 401 | TGACGCAGAT | GTTTACTGGT | GTGGGATTGA | AAGAAGAGGA CCTGACCTTG |
| 451 | GGACTCAAGT | GAAAATTGAT | TGTTNACCCA | GAGGGAGCGG CTTTCCACAA |
| 501 | CAGCAAAGCT | CACCTACCAA | CAGCAATATG | GCAGTGTTCA TCGGCTCCCA |
| 551 | CAAGAGGAAC | CACTACATGC | TCCTGGTATT | TGTGAAGGTG CCCATCTTGC |
| 601 | TCATCTTGGT | CAATGCCATN | CTCTGGTTGA | AAGGGTCTCA GAGGGTCCCT |
| 651 | GAGGAGCCAN | GGGAACAGCC | TATCTACATG | GACTTCTCCG GACTCTGACT |
| 701 | AAAGACAT | | | |

ᶜA partial nucleotide sequence of a human PIGR-1 (SEQ ID NO: 3).

TABLE 4ᵈ

| | | | | |
|---|---|---|---|---|
| 1 | MWLPPALLLL | SLSGCFSIQG | PESVRAPEQG | SLTVQCHYKQ GWETYIKWWC |
| 51 | RGVRWDTCKI | LIETRGSEQG | EKSDRVSIKD | NQKDRTFTVT MEGLRRDDAD |
| 101 | VYWCGIERRG | PDLGTQVKID | CXPRGSGFPQ | QQSSPTNSNM AVFIGSHKRN |
| 151 | HYMLLVFVKV | PILLILVNAX | LWLKGSQRVP | EEPXEQPIYM DFSGL |

ᵈA partial amino acid sequence of a human PIGR-1 (SEQ ID NO: 4).

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97-99% identity between the sequences.

Polynucleotides of the invention, which are identical or sufficiently identical to a nucleotide sequence contained in SEQ ID NO:1 or a fragment thereof, may be used as hybridization probes for cDNA and genomic DNA, to isolate full-length cDNAs and genomic clones encoding PIGR-1 and to isolate cDNA and genomic clones of other genes (including genes encoding homologs and orthologs from species other than human) that have a high sequence similarity to the PIGR-1 gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding PIGR-1 polypeptide, including homologs and orthologs from species other than human, comprises the steps of screening an appropriate library under stingent hybridization conditions with a labeled probe having the SEQ ID NO: 1 or a fragment thereof (including that of SEQ ID NO: 3), and isolating full-length cDNA and genomic clones containing said polynucleotide sequence. Such hybridization techniques are well known to those of skill in the art. Stringent hybridization conditions are as defined above or alternatively conditions under overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli*, *Streptomyces* and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the PIGR-1 polypeptide is to be expressed for use in screening assays, generally, it is preferred that the polypeptide be produced at the surface of the cell. In this event, the cells may be harvested prior to use in the screening assay. If PIGR-1 polypeptide is secreted into the medium, the medium can be recovered in order to recover and purify the polypeptide; if produced intracellularly, the cells must first be lysed before the polypeptide is recovered.

PIGR-1 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of PIGR-1 polynucleotides for use as diagnostic reagents. Detection of a mutated form of PIGR-1 gene associated with a dysfunction will provide a diagnostic tool that can add to or define a diagnosis of a disease or susceptibility to a disease which results from under-expression, over-expression or altered expression of PIGR-1. Individuals carrying mutations in the PIGR-1 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled PIGR-1 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985)230:1242. Sequence changes at specific locations may also be revealed by nuclease protection assays, such as RNase and S1 protection or the chemical cleavage method. See Cotton et al., *Proc Natl Acad Sci USA* (1985) 85: 4397–4401. In another embodiment, an array of oligonucleotides probes comprising PIGR-1 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., Science, Vol 274, pp 610–613 (1996)).

The diagnostic assays offer a process for diagnosing or determining a susceptibility to rheumatoid arthritis (RA), multiple sclerosis (MS), psoriasis, systemic lupus erythematosus (SLE) and inflammatory bowel disease (IBD) through detection of mutation in the PIGR-1 gene by the methods described.

In addition, rheumatoid arthritis (RA), multiple sclerosis (MS), psoriasis, systemic lupus erythematosus (SLE) and inflammatory bowel disease (IBD), can be diagnosed by methods comprising determining from a sample derived from a subject an abnormally decreased or increased level of PIGR-1 polypeptide or PIGR-1 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an PIGR-1, in a sample derived from a host are well-known to those of skill in the art. Such assay methods include radioimmunoassays, competitive-binding assays, Western Blot analysis and ELISA assays.

Thus in another aspect, the present invention relates to a diagonostic kit for a disease or suspectability to a disease, particularly rheumatoid arthritis (RA), multiple sclerosis (MS), psoriasis, systemic lupus erythematosus (SLE) and inflammatory bowel disease (IBD), which comprises:

(a) a PIGR-1 polynucleotide, preferably the nucleotide sequence of SEQ ID NO: 1, or a fragment thereof;

(b) a nucleotide sequence complementary to that of (a);

(c) a PIGR-1 polypeptide, preferably the polypeptide of SEQ ID NO: 2, or a fragment thereof; or (d) an antibody to a PIGR-1 polypeptide, preferably to the polypeptide of SEQ ID NO: 2.

It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the PIGR-1 polypeptides. The term "immunospecific" means that the antibodies have substantiall greater affinity for the polypeptides of the invention than their affinity for other related polypeptides in the prior art.

Antibodies generated against the PIGR-1 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against PIGR-1 polypeptides may also be employed to treat rheumatoid arthritis (RA), multiple sclerosis (MS), psoriasis, systemic lupus erythematosus (SLE) and inflammatory bowel disease (IBD), among others.

Vaccines

Another aspect of the invention relates to a method for inducing an immunological response in a mammal which comprises inoculating the mammal with PIGR-1 polypeptide, or a fragment thereof, adequate to produce antibody and/or T cell immune response to protect said animal from rheumatoid arthritis (RA), multiple sclerosis (MS), psoriasis, systemic lupus erythematosus (SLE) and inflammatory bowel disease (IBD), among others. Yet another aspect of the invention relates to a method of inducing immunological response in a mammal which comprises, delivering PIGR-1 polypeptide via a vector directing expression of PIGR-1 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a PIGR-1 polypeptide wherein the composition comprises a PIGR-1 polypeptide or PIGR-1 gene. The vaccine formulation may further comprise a suitable carrier. Since PIGR-1 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain antioxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The PIGR-1 polypeptide of the present invention may be employed in a screening process for compounds which bind the receptor and which activate (agonists) or inhibit activation of (antagonists) the receptor polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al., *Current Protocols in Immunology* 1(2):Chapter 5 (1991).

PIGR-1 polypeptides are responsible for many biological functions, including many pathologies. Accordingly, it is desirous to find compounds and drugs which stimulate PIGR-1 on the one hand and which can inhibit the function of PIGR-1 on the other hand. In general, agonists are employed for therapeutic and prophylactic purposes for such conditions as rheumatoid arthritis (RA), multiple sclerosis (MS), psoriasis, systemic lupus erythematosus (SLE) and inflammatory bowel disease (IBD) Antagonists may be employed for a variety of therapeutic and prophylactic purposes for such conditions as rheumatoid arthritis (RA), multiple sclerosis (MS), psoriasis, systemic lupus erythematosus (SLE) and inflammatory bowel disease (IBD)

In general, such screening procedures involve producing appropriate cells which express the receptor polypeptide of the present invention on the surface thereof Such cells include cells from mammals, yeast, Drosophila or *E. coli*. Cells expressing the receptor (or cell membrane containing the expressed receptor) are then contacted with a test compound to observe binding, or stimulation or inhibition of a functional response.

The assays may simply test binding of a candidate compound wherein adherence to the cells bearing the receptor is detected by means of a label directly or indirectly associated with the candidate compound or in an assay involving competition with a labeled competitor. Further, these assays may test whether the candidate compound results in a signal generated by activation of the receptor, using detection systems appropriate to the cells bearing the receptor at their surfaces. Inhibitors of activation are generally assayed in the presence of a known agonist and the effect on activation by the agonist by the presence of the candidate compound is observed.

Further, the assays may simply comprise the steps of mixing a candidate compound with a solution containing a PIGR-1 polypeptide to form a mixture, measuring PIGR-1 activity in the mixture, and comparing the PIGR-1 activity of the mixture to a standard.

The PIGR-1 cDNA, protein and antibodies to the protein may also be used to configure assays for detecting the effect of added compounds on the production of PIGR-1 mRNA and protein in cells. For example, an ELISA may be constructed for measuring secreted or cell associated levels of PIGR-1 protein using monoclonal and polyclonal antibodies by standard methods known in the art, and this can be used to discover agents which may inhibit or enhance the production of PIGR-1 (also called antagonist or agonist, respectively) from suitably manipulated cells or tissues. Standard methods for conducting screening assays are well understood in the art.

Examples of potential PIGR-1 antagonists include antibodies or, in some cases, oligonucleotides or proteins which are closely related to the ligand of the PIGR-1, e.g., a fragment of the ligand, or small molecules which bind to the receptor but do not elicit a response, so that the activity of the receptor is prevented.

Thus in another aspect, the present invention relates to a screening kit for identifying agonists, antagonists, ligands, receptors, substrates, enzymes, etc. for PIGR-1 polypeptides; or compounds which decrease or enhance the production of PIGR-1 polypeptides, which comprises:

(a) a PIGR-1 polypeptide, preferably that of SEQ ID NO:2;

(b) a recombinant cell expressing a PIGR-1 polypeptide, preferably that of SEQ ID NO:2;

(c) a cell membrane expressing a PIGR-1 polypeptide; preferably that of SEQ ID NO: 2; or (d) antibody to a PIGR-1 polypeptide, preferably that of SEQ ID NO: 2.

It will be appreciated that in any such kit, (a), (b), (c) or (d) may comprise a substantial component.

Prophylactic and Therapeutic Methods

This invention provides methods of treating an abnormal conditions related to both an excess of and insufficient amounts of PIGR-1 activity.

If the activity of PIGR-1 is in excess, several approaches are available. One approach comprises administering to a subject an inhibitor compound (antagonist) as hereinabove described along with a pharmaceutically acceptable carrier in an amount effective to inhibit activation by blocking binding of ligands to the PIGR-1, or by inhibiting a second signal, and thereby alleviating the abnormal condition.

In another approach, soluble forms of PIGR-1 polypeptides still capable of binding the ligand in competition with endogenous PIGR-1 may be administered. Typical embodiments of such competitors comprise fragments of the PIGR-1 polypeptide.

In still another approach, expression of the gene encoding endogenous PIGR-1 can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991)251:1360. These oligomers can be administered per se or the relevant oligomers can be expressed in vivo.

For treating abnormal conditions related to an underexpression of PIGR-1 and its activity, several approaches are also available. One approach comprises administering to a subject a therapeutically effective amount of a compound which activates PIGR-1, i.e., an agonist as described above, in combination with a pharmaceutically acceptable carrier, to thereby alleviate the abnormal condition. Alternatively, gene therapy may be employed to effect the endogenous production of PIGR-1 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996).

Formulation and Administration

Peptides, such as the soluble form of PIGR-1 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 µg/kg of subject. Wide variations in the needed dosage, however, are to be expected in view of the variety of compounds available and the differing efficiencies of various routes of administration. For example, oral administration would be expected to require higher dosages than administration by intravenous injection.

Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Example 2

PIGR-1 Belongs to Immunoglobulin (Ig) Superfamily

The extracellular region of PIGR-1 contains a single Ig domain with a V-like fold as shown by (1) the presence of Ig V fold conserved residues and (2) homology to several other Ig like proteins (poly Ig V1 and V4, CMRF35, TCR Vβ and Ig κ $V_L$).

In the following alignment, conserved Ig V residues are shown in bold and residues in PIGR-1 shared with at least 3 of the other members are noted with a *.

```
                        B              C          C'    C"
                       ___            ___        ___   __                (AA 18-75 OF
PIGR-1      IQGPESVRAPEQGSLTVQCHYKQGWETYIKWWC..RGVRWDTCKILIETRGSEQGEKSDR 75  SEQ ID NO:2)

PolyIgRV1   IFGPEEVNSVEGNSVSITCYYPPTSVNTRKYWC.RQGARG..CITLISSEGYVSSKYAGR 57  (SEQ ID NO:5)

PolyIgRV4   PRSPTVVKGVAGSSVAVLCPYNRKESKSIKYWCLWEGAQNGRCPLLVDSEGWVKAQYEGR 60  (SEQ ID NO:6)

CMRF35      LSHPMTVAGPVGGSLSVQCRYEKEHRTLNKFWC..RPPQILRCDKIVETKGS.AGKRNGR 56  (SEQ ID NO:7)

TCR Vβ       SQKPSRDICQRGTSLTIQCQV.DSQVTMMFWYRQQPGQSLTLIATANQGSEATYESGFVI 60  (SEQ ID NO:8)

Ig κ $V_L$   TQTPASVEVAVGGTVTIKCQASQSISTYLSWYQQKPGQRPKLLIY....RASTLASG.VS 56  (SEQ ID NO:9)
               *  *     * * *    *  **  *      *       *      *

D         E              F
                       ___      _____           ___                      (AA 76-121 of
PIGR-1      VSIKDNQKDRTF.TVTMEGLRRDDADVYWCGIERRGPDLGTQVKVIV                  SEQ ID NO:2)

PolyIgRVI   ANLTNFPENGTF.TVILNQLSQDDSGRYKCGLGINSRGLSFDVSLEV                  (SEQ ID NO:10)

PolyIgV4    LSLLEEPGNGTF.TVILNQLTSRDAGFYWC...LTNGDTLWRTTVEI                  (SEQ ID NO:11)

CMRF35      VSIRDSPANLSF.TVTLENLTEEDAGTYWCGVDTPWLRDFHDPIVEV                  (SEQ ID NO:12)

TCR Vβ       DKFPISRPNLTFSTLTVSNMSPEDSSIYLCSVE..GEAGDTQY.FGP                  (SEQ ID NO:13)

Ig κ $V_L$   SRFKGSGSGTEF.TLTISGVECADAATYYCQQGWSSSNVEN...VFG                  (SEQ ID NO:14)
               ** ***  *  **  * *                *
```

EXAMPLES

The examples below are carried out using standard techniques, which are well known and routine to those of skill in the art, except where otherwise described in detail. The examples illustrate, but do not limit the invention.

Example 1

While there are several methods to obtain the full length cDNA, two are outlined below.

1) The method of Rapid Amplification of cDNA Ends (RACE) can be utilized to obtain the 5' end. See Frohman et al., Proc. Nat. Acad. Sci USA 85, 8998–9002. (1988). Briefly, specific oliognucleotides are annealed to mRNA and used to prime the synthesis of the cDNA strand. Following destruction of the mRNA with RNaseH, a poly C anchor sequence is added to the 3' end of the cDNA and the resulting fragment is amplified using a nested set of antisense primers and an anchor sequence primer. The amplified fragment is cloned into an appropriate vector and subjected to restriction and sequence analysis.

2) The polymerase chain reaction can be used to amplify the 5' end of the cDNA from human cDNA libraries using sequential rounds of nested PCR with two sets of primers. One set of antisense primers is specific to the 5' end of the partial cDNA and the other set of primers anneals to a vector specific sequence. The amplified products are cloned into an appropriate vector and subjected to restriction and sequence analysis.

Example 3

PIGR-1 Gene Expression Pattern

PIGR-1, a new member of the Ig superfamily, has been identified. The predicted protein sequence of this new gene shows modest, but extended, homology to CMRF-35, particularly in the extracellular domain. Based on the library source of the EST sequences comprising PIGR-1 which were isolated from leucocytes such as macrophage, neutrophil, eosinophil and T cells, its expression is restricted to leucocytes, suggesting a role in immune function. Thus, this protein is a candidate target for diseases of the immune system such as rheumatoid arthritis (RA), multiple sclerosis (MS), psoriasis, systemic lupus erythematosus (SLE) and inflammatory bowel disease (IBD)

Example 4

Recombinant Soluble PIGR-1 Proteins

The extracellular domain of PIGR-1 is expressed as a secreted soluble protein by truncation at the start of the transmembrane domain (asparagine 149 or histidine 150 in Table 2) as has been described for other immunoglobulin domain proteins, e.g. for CD4 (K. C. Deen et al., Nature 331: 82–84 (1988)). PIGR-1 is also expressed as a secreted, soluble Ig fusion protein by linking the same extracellular region of PIGR-1 to the hinge and constant domains of heavy chain IgG such as has been described for CD4 (D. J.

Capon et al., Nature 317: 525–531 (1989)). In addition, preparation of oligomeric Ig fusion proteins is possible by addition of the tailpiece segment of IgM or IgA to the C-terminus of the Fc domain of IgGs, as exemplified for the IgM tailpiece segment in R. I. F. Smith and S. L. Morrison, Biotechnology 12: 683–688 (1994) and in R. I. F. Smith, et al., J. Immunol. 154: 2226–2236 (1995). These proteins are produced in insect cells or in mammalian cells such as COS-7 or CHO, purified by standard methodology, and are useful as tool, therapeutic, and diagnostic agents. Thus, these proteins are used to:

a) Determine the cleavage site of the N-terminal leader by amino acid sequence analysis of this processed recombinant protein.

b) Prepare polyclonal and monoclonal antibodies for:

1) Detection of PIGR-1 protein expression in different tissues and cell types.
2) Functional studies of PIGR-1 protein, such as induction of cell differentiation and proliferation, cytokine production, and cell death assays.

c) Test for agonist/antagonist activity when added to cultured cells and in animal models of immune disease.

d) Search for its ligand(s).

e) Establish screen assays for small molecule agonists or antagonists of PIGR-1 protein, which may be potential therapeutic and/or diagnostic agents.

All publications, including but not limited to patents and patent applications, cited in this specification are herein incorporated by reference as if each individual publication were specifically and individually indicated to be incorporated by reference herein as though fully set forth.

What is claimed is:

1. An isolated polynucleotide comprising a nucleotide sequence encoding the amino acid sequence set forth in SEQ ID NO:2.

2. The isolated polynucleotide of claim 1 wherein said polynucleotide comprises the nucleotide sequence of SEQ ID NO:1 encoding the PIGR-1 polypeptide of SEQ ID NO: 2.

3. An isolated polynucleotide comprising the nucleotide sequence of SEQ ID NO: 1.

4. The isolated polynucleotide of any one of claims 1, 2, or 3 which is DNA or RNA.

5. An expression system comprising an isolated DNA or RNA molecule, wherein said expression system is capable of producing a PIGR-1 polypeptide comprising an amino acid sequence as set forth in SEQ ID NO:2 when said expression system is present in a compatible host cell.

6. An isolated host cell comprising the expression system of claim 5.

7. A process for producing a PIGR-1 polypeptide comprising culturing an isolated host cell of claim 6 under conditions sufficient for the production of said polypeptide and recovering the polypeptide from the culture.

8. A process for producing a recombinant host cell which produces a PIGR-1 polypeptide thereof comprising transforming or transfecting a host cell with the expression system of claim 5 such that the isolated host cell, under appropriate culture conditions, produces a PIGR-1 polypeptide.

9. A recombinant host cell produced by the process of claim 8.

10. The isolated polynucleotide of claim 1 wherein said polynucleotide sequence is the entire length of the RNA transcript of SEQ ID NO: 1.

11. The isolated polynucleotide of claim 1 wherein said polynucleotide sequence is the coding region of the RNA transcript of SEQ ID NO: 1.

12. The isolated polynucleotide of claim 1 comprising a nucleotide sequence encoding at least 50 contiguous amino acids from the amino acid sequence set forth in SEQ ID NO:2.

13. The isolated polynucleotide of claim 1 comprising a nucleotide sequence encoding at least 100 contiguous amino acids from the amino acid sequence set forth in SEQ ID NO: 2.

14. The isolated polynucleotide of claim 1 comprising a nucleotide sequence encoding at least 200 contiguous amino acids from the amino acid sequence set forth in SEQ ID NO: 2.

15. The isolated polynucleotide of claim 1 comprising a nucleotide sequence encoding at least 300 contiguous amino acids from the amino acid sequence set forth in SEQ ID NO: 2.

16. The isolated polynucleotide of claim 1 comprising a nucleotide sequence encoding at least 400 contiguous amino acids from the amino acid sequence set forth in SEQ ID NO: 2.

17. A polynucleotide sequence which is completely complementary to any of the isolated polynucleotides in any one of claims 1, 3, 10–15 or 16.

18. An isolated polynucleotide obtainable by screening an appropriate library under stringent conditions of overnight incubation at 42° C. in a solution comprising: 50% formamide, 5×SSC (150 mM NaCl, 15 mM trisodium salt, 50 mM sodium phosphate, pH 7.6), 5×Denhardt's solution, 10% dextran sulfate, and 20 μg/ml denatured, sheared salmon sperm DNA, followed by washing in 0.1×SSC at 65° C., with a probe having the sequence of SEQ ID NO: 1.

* * * * *